US009375199B2

(12) United States Patent
Kang et al.

(10) Patent No.: US 9,375,199 B2
(45) Date of Patent: Jun. 28, 2016

(54) ULTRASONIC IMAGING APPARATUS AND IMAGE DISPLAY METHOD THEREOF

(71) Applicant: SAMSUNG ELECTRONICS CO., LTD., Suwon-si (KR)

(72) Inventors: Joo Young Kang, Yongin-si (KR); Kyu Hong Kim, Seongnam-si (KR); Jung Ho Kim, Yongin-si (KR); Sung Chan Park, Suwon-si (KR); Su Hyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 139 days.

(21) Appl. No.: 14/271,853

(22) Filed: May 7, 2014

(65) Prior Publication Data
US 2014/0336509 A1 Nov. 13, 2014

(30) Foreign Application Priority Data
May 7, 2013 (KR) ........................ 10-2013-0051532

(51) Int. Cl.
*A61B 8/14* (2006.01)
*A61B 8/08* (2006.01)
*A61B 8/00* (2006.01)

(52) U.S. Cl.
CPC ............. *A61B 8/5292* (2013.01); *A61B 8/4444* (2013.01); *A61B 8/4483* (2013.01); *A61B 8/5207* (2013.01); *A61B 8/5246* (2013.01); *A61B 8/0883* (2013.01); *A61B 8/4405* (2013.01); *A61B 8/483* (2013.01)

(58) Field of Classification Search
CPC .. A61B 8/0883; A61B 8/4405; A61B 8/4444; A61B 8/4483; A61B 8/483; A61B 8/5207; A61B 8/5246; A61B 8/5292
See application file for complete search history.

(56) References Cited

U.S. PATENT DOCUMENTS

| 2004/0193053 | A1 | 9/2004 | Kato |
| 2006/0184019 | A1 | 8/2006 | Ito et al. |
| 2006/0253030 | A1 | 11/2006 | Altmann et al. |
| 2008/0137927 | A1 | 6/2008 | Altmann et al. |
| 2008/0187193 | A1 | 8/2008 | Hoctor et al. |
| 2010/0016716 | A1 | 1/2010 | Hyun |

FOREIGN PATENT DOCUMENTS

JP 10-295693 A 11/1998

*Primary Examiner* — Mark Remaly
(74) *Attorney, Agent, or Firm* — Sughrue Mion, PLLC

(57) ABSTRACT

Disclosed herein are an ultrasonic imaging apparatus and an image display method thereof. The ultrasonic imaging apparatus includes an ultrasonic probe configured to transmit ultrasonic signals toward an object and to receive ultrasonic signals reflected by the object, a beamformer configured to perform beamforming based on the ultrasonic signals received by the ultrasonic probe, and an image processor configured to generate an ultrasonic image of an examined region within the object based on the beamforming, to extract characteristic information which relates to the examined region from the generated ultrasonic image, and to judge whether or not the examined region coincides with a target region based on the extracted characteristic information, thus facilitating a determination as to with which region within the object the examined region corresponds based on various pieces of the characteristic information of the examined region extracted via analysis of the ultrasonic image.

10 Claims, 10 Drawing Sheets

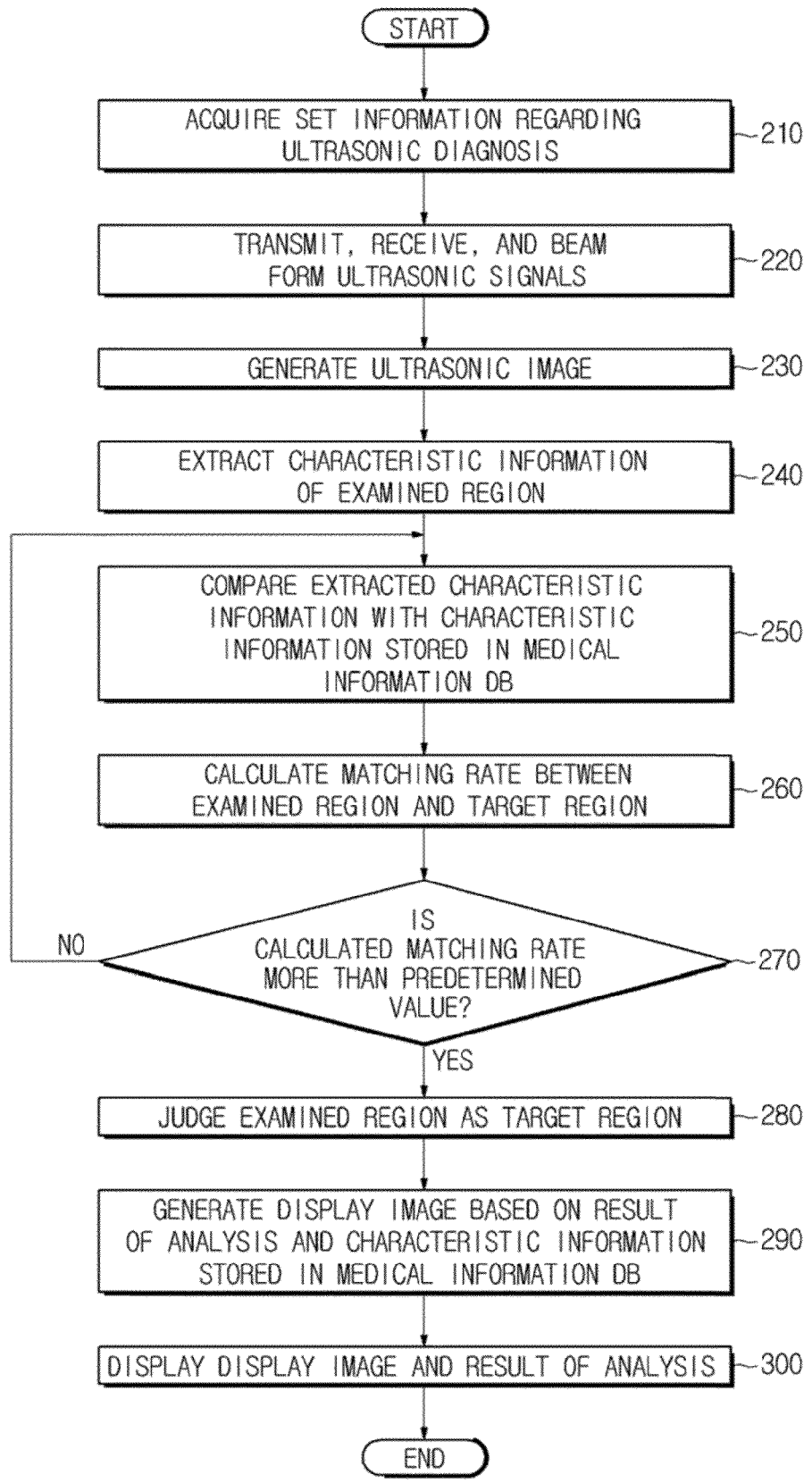

ULTRASONIC IMAGING APPARATUS AND IMAGE DISPLAY METHOD THEREOF

CROSS-REFERENCE TO RELATED APPLICATION

This application claims priority from Korean Patent Application No. 10-2013-0051532, filed on May 7, 2013 in the Korean Intellectual Property Office, the disclosure of which is incorporated herein by reference in its entirety.

BACKGROUND

1. Field

Exemplary embodiments relate to an ultrasonic imaging apparatus and an image display method thereof which are usable for generating an image of the inside of an object by using ultrasonic waves.

2. Description of the Related Art

In general, an ultrasonic imaging apparatus collects information regarding the inside of an object (for example, a human body) by using ultrasonic waves, and acquires an image of the inside of the object by using the collected information.

In particular, the ultrasonic imaging apparatus may collect ultrasonic waves which are reflected or generated by a target region within the object, and acquire tomographic images of various structures and/or tissues, for example, tomographic images of various organs or soft tissues, within the object, by using the collected ultrasonic waves. For this purpose, the ultrasonic imaging apparatus may irradiate ultrasonic waves toward the target region within the object from the outside of the object, and collect ultrasonic waves which are reflected by a target point within the object.

The ultrasonic imaging apparatus generates ultrasonic waves of a designated frequency by using ultrasonic transducers, etc., irradiates the ultrasonic waves of the designated frequency toward a target point, and receives ultrasonic waves which are reflected by the target point, thus acquiring ultrasonic signals of a plurality of channels which correspond to the received ultrasonic waves. The ultrasonic imaging apparatus may acquire beamformed ultrasonic signals by correcting and focusing time differences among the ultrasonic signals of the plurality of channels, and generate and acquire ultrasonic images by using the beamformed ultrasonic signals so that a user may confirm sectional plane images within the object.

Such an ultrasonic imaging apparatus is small and inexpensive, as compared to other apparatuses, may reproduce an image within an object in real time, and have none of the dangers of radiation exposure, thus being widely used in various fields, such as the medical world.

In general, a 2D ultrasonic image or a 3D ultrasonic image of an object may be acquired through the ultrasonic imaging apparatus. 2D ultrasonic imaging is mainly used now, but increasingly, 3D ultrasonic imaging is being used to perform volume quantification or accurate diagnosis and treatment of an object. In order to acquire a 3D ultrasonic image, ultrasonic transducers aligned in a 2D array are commercially used, and many trials to reduce cost and weight have been carried out through the use of capacitive micromachined ultrasonic transducers (cMUT). Through such development, it is predicted that use of ultrasonic imaging apparatuses will gradually increase.

In order to generalize these ultrasonic imaging apparatuses, a guide system within an ultrasonic imaging apparatus is required in order to enable the general public to easily use the apparatus. A sonographer, who has anatomical knowledge and a well-honed measuring technique through extensive experience, may easily judge to which organ or region a 3D image of an organ expressed through ultrasonic imaging corresponds, and thereby easily detect lesions. Conversely, a general user who is unfamiliar with use of the ultrasonic imaging apparatus or ultrasonic reading may lack fundamental anatomical knowledge regarding positions and shapes of organs, and thus may fail to execute an ultrasonic diagnosis or may miss important lesions, and therefor needs to master various pieces of anatomical knowledge of respective organs in order to properly execute an ultrasonic diagnosis.

SUMMARY

Therefore, it is an aspect of one or more exemplary embodiments to provide an ultrasonic imaging apparatus and an image display method thereof which may be easily used by a general user that lacks anatomical knowledge and/or measuring techniques, as well as by a sonographer.

It is another aspect of one or more exemplary embodiments to provide an ultrasonic imaging apparatus and an image display method thereof which may be used to more accurately judge to which region within an object an examined region corresponds based on various pieces of characteristic information which relate to the examined region and which are extracted via analysis of an ultrasonic image.

Additional aspects of the exemplary embodiments will be set forth in part in the description which follows and, in part, will be obvious from the description, or may be learned by practice of the exemplary embodiments.

In accordance with one aspect of one or more exemplary embodiments, an ultrasonic imaging apparatus includes an ultrasonic probe configured to transmit ultrasonic signals toward an object and to receive ultrasonic signals reflected by the object, a beamformer configured to perform beamforming based on the ultrasonic signals received by the ultrasonic probe, and an image processor configured to generate an ultrasonic image of an examined region within the object based on a result of the beamforming, to extract characteristic information which relates to the examined region from the generated ultrasonic image, and to judge whether or not the examined region coincides with a target region based on the extracted characteristic information.

The examined region may include a region which corresponds to a target of a diagnosis which is imaged by using the ultrasonic probe, and the target region may include a region which is set by a user.

The ultrasonic imaging apparatus may further include a medical information database configured to store at least one from among standardized ultrasonic images of a plurality of regions within the object, standardized X-ray images, magnetic resonance imaging (MRI) images and computed tomography (CT) images of the plurality of regions within the object, first characteristic information which relates to the plurality of regions within the object, and second characteristic information which relates to a plurality of lesions and which is usable for detecting one or more lesions which are present in the examined region within the target object.

The first characteristic information may include at least one from among a shape of one or more of the plurality of regions, a sound velocity of at least one ultrasonic wave reflected by one or more of the plurality of regions, and a degree of elasticity of one or more of the plurality of regions.

The imaging processor may include an image generator configured to generate at least one from among a two-dimensional (2D) ultrasonic image and a three-dimensional (3D)

ultrasonic image of the examined region based on the result of the beamforming, a characteristic information extractor configured to extract third characteristic information which relates to the examined region by performing analysis of the generated at least one from among the 2D ultrasonic image and the 3D ultrasonic image of the examined region, and an examined region analyzer configured to judge whether or not the examined region coincides with the target region by comparing the extracted third characteristic information which relates to the examined region with the first characteristic information which relates to the target region and which is stored in the medical information database.

The examined region analyzer may be further configured to calculate a matching rate between the examined region and the target region based on a result of the comparing of the third characteristic information with the first characteristic information, and to judge that the examined region coincides with the target region if the calculated matching rate is greater than a predetermined value.

The examined region analyzer may be further configured to divide the examined region into a plurality of areas based on the extracted third characteristic information which relates to the examined region.

The examined region analyzer may be further configured to detect at least one lesion which is present in the examined region based on the extracted third characteristic information which relates to the examined region.

The image processor may further include a display image generator configured to generate a display image based on a result of the judging as to whether or not the examined region coincides with the target region, the examined region divided into the plurality of areas, a result of the detecting of the at least one lesion, and various pieces of information which is stored in the medical information database.

The ultrasonic imaging apparatus may further include a display component configured to display the display image, and the display component may include a first medical image display region configured to display at least one from among a standardized X-ray image, an MRI image, and a CT image of the examined region judged as the target region, a guide image display region configured to display a guide image so as to facilitate a use of the ultrasonic probe with respect to the target region, a reference ultrasonic image display region configured to display a reference ultrasonic image of the target region so as to facilitate a comparison with a currently acquired real-time ultrasonic image, a current ultrasonic image display region configured to display the currently acquired real-time ultrasonic image, and an analysis result display region configured to display a result of the judging performed by the examined region analyzer.

In accordance with another aspect of one or more exemplary embodiments, an image display method which is executable by an ultrasonic imaging apparatus which includes an ultrasonic probe configured to transmit ultrasonic signals toward an object and to receive ultrasonic signals reflected by the object, a beamformer configured to perform beamforming based on the ultrasonic signals received by the ultrasonic probe, and a medical information database configured to store at least one from among standardized ultrasonic images of a plurality of regions within the object, standardized X-ray images, MRI images and CT images of the plurality of regions within the object, first characteristic information which relates to the plurality of regions within the object, and second characteristic information which relates to a plurality of lesions and which is usable for detecting one or more lesions which are present in an examined region within the target object, includes generating at least one from among a 2D ultrasonic image and a 3D ultrasonic image of the examined region within the object based on a result of the beamforming, extracting third characteristic information which relates to the examined region from the generated at least one from among the 2D ultrasonic image and the 3D ultrasonic image, and judging whether or not the examined region coincides with a target region based on the extracted third characteristic information.

The examined region may include a region which corresponds to a target of diagnosis which is imaged by using the ultrasonic probe, and the target region may include a region which is set by a user.

The first characteristic information may include at least one from among a shape of at least one from among the plurality of regions, a sound velocity of at least one ultrasonic wave reflected by at least one from among the plurality of regions, and a degree of elasticity of at least one from among the plurality of regions.

The judging whether or not the examined region coincides with the target region based on the extracted third characteristic information may include comparing the extracted third characteristic information which relates to the examined region with the first characteristic information which relates to the target region and which is stored in the medical information database.

The image display method may further include generating a display image based on a result of the judging whether or not the examined region coincides with the target region and various pieces of information stored in the medical information database.

The image display method may further include displaying the generated display image and a result of the judging whether or not the examined region coincides with the target region.

BRIEF DESCRIPTION OF THE DRAWINGS

These and/or other aspects will become apparent and more readily appreciated from the following description of exemplary embodiments, taken in conjunction with the accompanying drawings of which:

FIG. 10 is a flowchart which illustrates an image display method of an ultrasonic imaging apparatus, in accordance with one exemplary embodiment.

DETAILED DESCRIPTION

Figure 1:
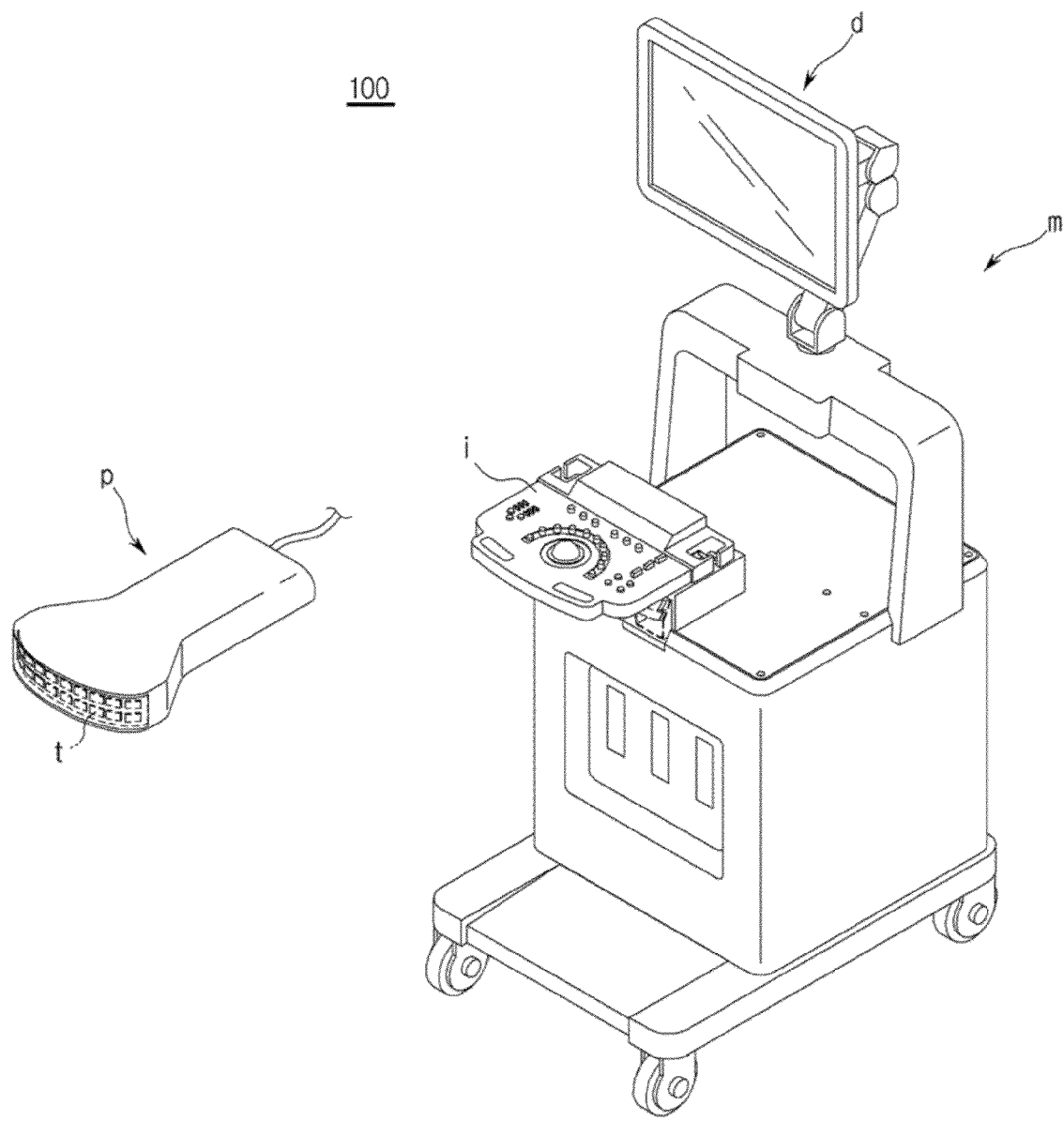
FIG. 1 is a perspective view which illustrates an external appearance of an ultrasonic imaging apparatus, in accordance with one exemplary embodiment.

Reference will now be made in detail to exemplary embodiments, examples of which are illustrated in the accompanying drawings, wherein like reference numerals refer to like elements throughout.

FIG. 1 is a perspective view which illustrates an external appearance of an ultrasonic imaging apparatus, in accordance with an exemplary embodiment.

An ultrasonic imaging apparatus is an imaging apparatus which transmits ultrasonic waves toward a target region within an object, for example, a human body, from the surface of the object, receives ultrasonic waves (i.e., ultrasonic echo waves) reflected by the target region, and generates tomographic images of various tissues or structures within the object by using the received ultrasonic information. As exemplarily shown in FIG. 1, an ultrasonic imaging apparatus 100 may include an ultrasonic probe p which is configured to transmit ultrasonic waves toward an object, to receive ultrasonic echo waves from the object, and to convert the ultrasonic echo waves into electrical signals, i.e., ultrasonic wave signals, and a main body m which is connected to the probe p and which includes an input unit (also referred to herein as an "input device") i and a display unit (also referred to herein as a "display component") d. A plurality of ultrasonic transducers t are arranged at the end of the ultrasonic probe p.

Figure 2:
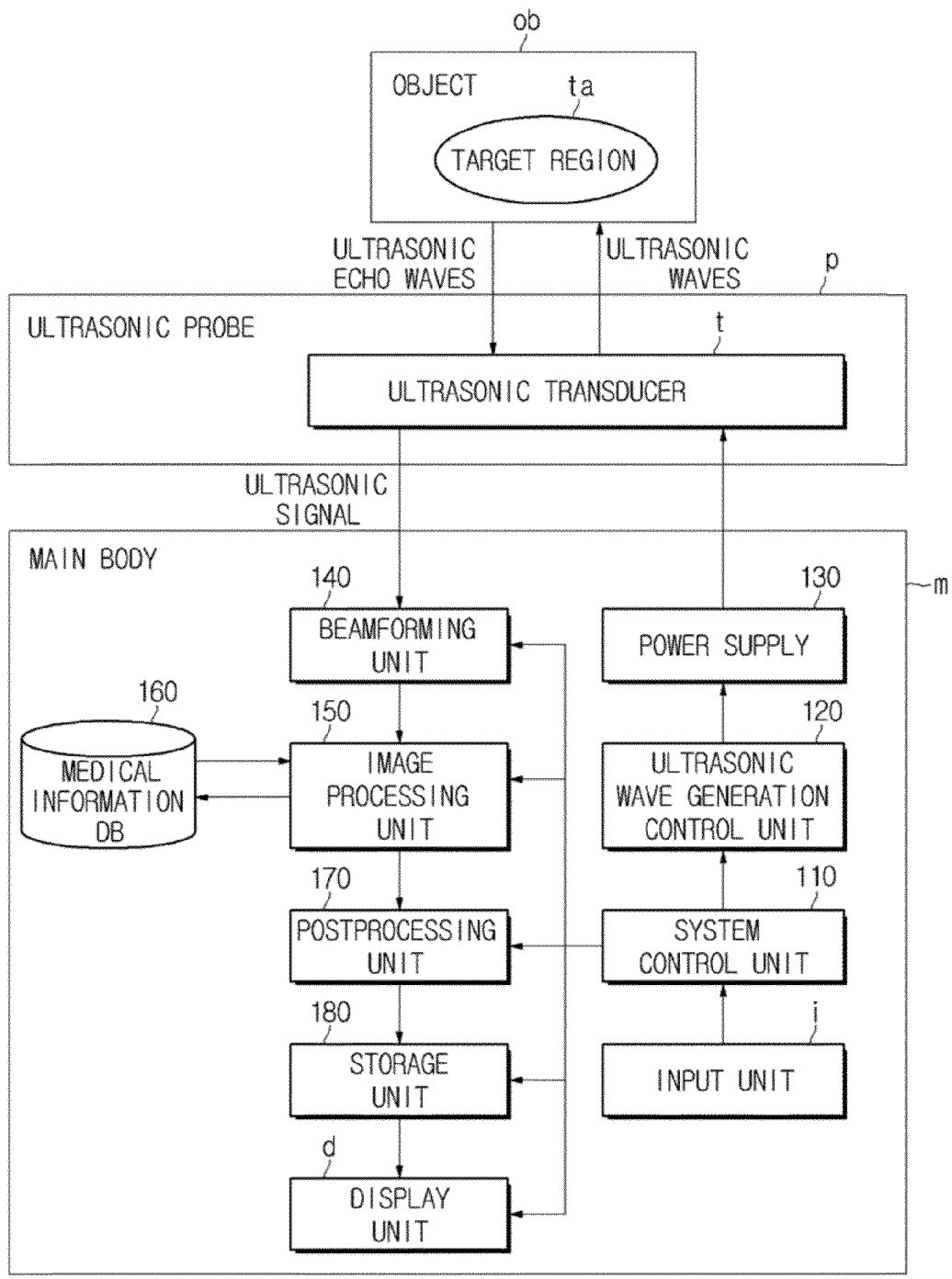
FIG. 2 is a control block diagram of the ultrasonic imaging apparatus.
Figure 3:
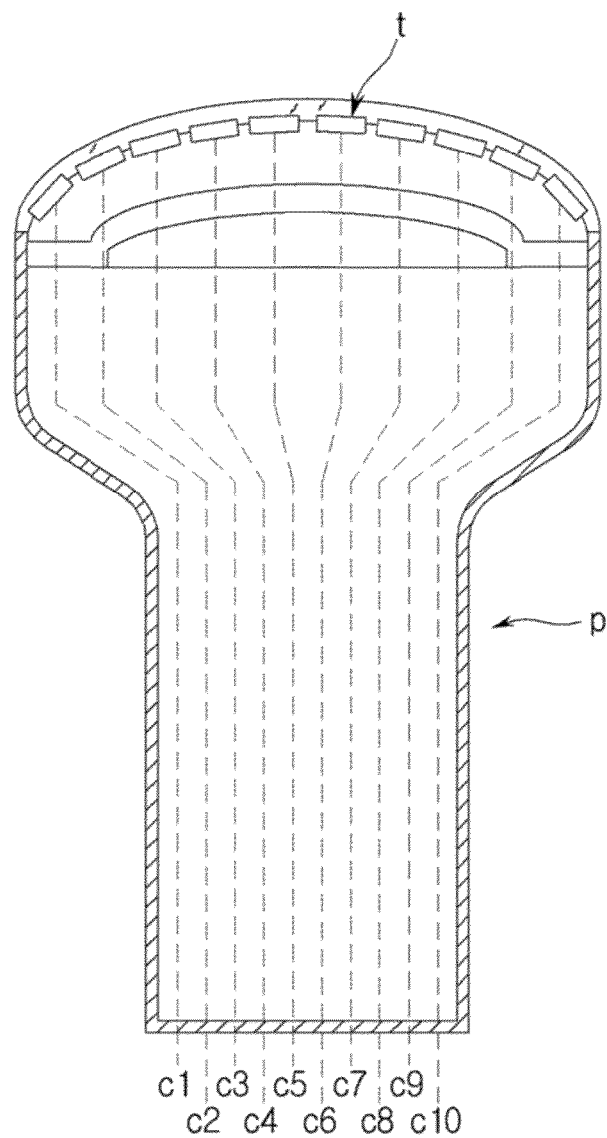
FIG. 3 is a plan view of an ultrasonic probe shown in FIG. 2.

FIG. 2 is a control block diagram of the ultrasonic imaging apparatus, and FIG. 3 is a plan view of the ultrasonic probe shown in FIG. 2.

As exemplarily shown in FIGS. 2 and 3, the ultrasonic probe p may include at least one ultrasonic transducer t which is configured to generate ultrasonic waves based on an applied voltage (or current), to transmit the generated ultrasonic waves toward at least one target region to within an object ob, to receive ultrasonic echo waves reflected by the at least one target region of the object ob, and to convert the received ultrasonic echo waves into an electrical signal. As exemplarily shown in FIG. 3, the at least one ultrasonic transducer t may be installed at one end of the ultrasonic probe b. In this case, the at least one ultrasonic transducer t may be aligned in at least one column at one end of the ultrasonic probe p.

A "transducer" refers to a device which converts one form of energy into another form of energy. In particular, the ultrasonic transducer t may convert electrical energy into wave energy, and vice versa. Therefore, the ultrasonic transducer t may perform both the function of an ultrasonic wave generating device and the function of an ultrasonic wave receiving device.

The ultrasonic transducer t generates ultrasonic waves while vibrating by using a pulse signal or an alternating-current (AC) current which is applied to the ultrasonic transducer t based on a control signal which is outputted by an ultrasonic wave generation control unit (also referred to herein as an "ultrasonic wave generation controller") 120 which is installed in the ultrasonic probe b or the main body m. The generated ultrasonic waves are transmitted to the target region ta within the object ob. In this case, the ultrasonic waves generated by the ultrasonic transducer t may be focused and transmitted toward a plurality of target regions ta within the object ob. In particular, the generated ultrasonic waves may be multi-focused and transmitted toward the plural target regions ta.

The ultrasonic waves generated by the ultrasonic transducer t are reflected by at least one target region ta within the object ob, and the reflections return to the ultrasonic transducer t. The ultrasonic transducer t receives ultrasonic echo waves which are reflected by the at least one target region ta. When the ultrasonic echo waves reach the ultrasonic transducer t, the ultrasonic transducer t vibrates at a designated frequency which corresponds to the frequency of the ultrasonic echo waves, and outputs an AC current of the frequency which corresponds to the vibrating frequency of the ultrasonic transducer t. Thereby, the ultrasonic transducer t may convert the received ultrasonic echo waves into a designated electrical signal.

Because each ultrasonic transducer t receives ultrasonic waves from the outside and outputs an electrical signal, the ultrasonic probe b may output electrical signals c1 to c10 of a corresponding plurality of channels, as exemplarily shown in FIG. 3. In this case, the number of the channels may be, for example, 64 or 128.

The ultrasonic transducer t may include a piezoelectric vibrator and/or a thin film. If an external power supply device or an internal electricity storage device, such as, for example, a power supply 130, such as a battery, applies an AC current to the piezoelectric vibrator or the thin film of the ultrasonic transducer t, the piezoelectric vibrator or the thin film vibrates at a designated frequency based on the applied AC current, and ultrasonic waves of a designated frequency are generated based on the vibrating frequency. Conversely, when ultrasonic echo waves of a designated frequency reach a piezoelectric material or the thin film, the piezoelectric material or the thin film vibrates based on the ultrasonic echo waves. In particular, the piezoelectric material or the thin film outputs an AC current of a frequency which corresponds to the vibrating frequency.

The ultrasonic transducer t may include at least one of, for example, a magnetostrictive ultrasonic transducer which uses the magnetostrictive effect of a magnetic material, a piezoelectric ultrasonic transducer which uses the piezoelectric effect of a piezoelectric material, and a capacitive micromachined ultrasonic transducer (cMUT) which transmits and receives ultrasonic waves by using vibrations of hundreds or thousands of micromachined thin films. Alternatively, the ultrasonic transducer t may include any one or more of other kinds of transducers which may generate ultrasonic waves based on an electrical signal or generate an electrical signal based on ultrasonic waves.

Further, the ultrasonic transducers 1 may be configured in a one-dimensional (1D) ultrasonic transducer array in which a plurality of ultrasonic transducers t1 to t10 (with reference to FIG. 4) are aligned one-dimensionally, i.e., in a line, or be configured in a 2D ultrasonic transducer array in which a plurality of ultrasonic transducers are aligned 2-dimensionally, i.e., in a plane.

The main body m, as exemplarily shown in FIG. 2, includes a system control unit (also referred to herein as a "system controller") 110, the ultrasonic wave generation control unit 120, the power supply 130, a beamforming unit (also referred to herein as a "beamformer") 140, an image processing unit (also referred to herein as an "image processor") 150, a medical information database 160, a postprocessing unit (also referred to herein as a "postprocessor") 170, a storage unit (also referred to herein as a "storage device" and/or as a "storage") 180, the input unit i, and the display unit d.

The system control unit 110 controls the overall operation of the main body m. In particular, the system control unit 110 may generate designated control signals which are directed to the ultrasonic probe p and the respective elements of the main body m, for example, the ultrasonic wave generation control unit 120, the beamforming unit 140, the image processing unit 150, the postprocessing unit 170, the storage unit 180, and the display unit d, so as to control the operation of the ultrasonic probe p and the respective elements of the main body m.

More particularly, the system control unit 110 may generate designated control instructions which are directed to the respective elements of the main body m in accordance with predetermined settings or directions or instructions of a user input which is received via the separate input unit i, thus controlling the ultrasonic imaging apparatus 100.

The ultrasonic wave generation control unit 120 may receive designated control instructions from the system control unit 110, generate a designated control signal based on the received control instructions, and transmit the generated control signal to the ultrasonic transducers t of the ultrasonic probe p. In this case, the ultrasonic transducers t may be operated in accordance with the received control signal and thus generate ultrasonic waves. Further, the ultrasonic wave generation control unit 120 may generate a control signal which relates to the power supply 130 electrically connected to the ultrasonic transducers t based on the received control instructions, and transmit the generated control signal to the power supply 130. In this case, the power supply 130, having received the control signal, may apply an AC current of a designated frequency to the ultrasonic transducers t based on the control signal, so that the ultrasonic transducers t may generate ultrasonic waves of a frequency which corresponds to the frequency of the AC current.

The beamforming unit 140 performs beamforming based on ultrasonic signals $c_1$ to $c_{10}$ of a plurality of channels, which signals are transmitted from the ultrasonic transducers t. In particular, "beamforming" refers to an increase of the intensity of signals through superposition when the signals are transmitted and received using a plurality of transducers. More particularly, beamforming refers to an acquisition of a proper ultrasonic image of the inside of the object ob by focusing a plurality of received signals which are input to a plurality of channels. The detailed configuration and operation of the beamforming unit 140 will be described below in detail with reference to FIG. 4.

Figure 5:
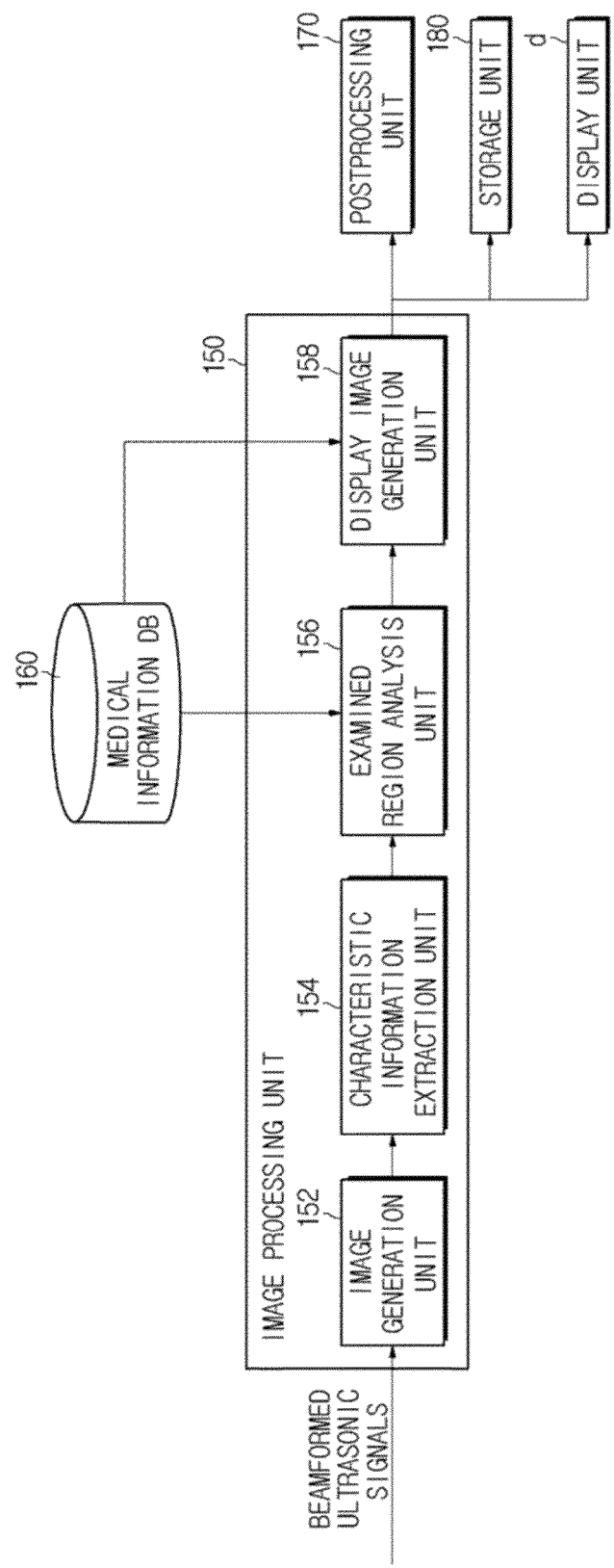
FIG. 5 is a view which illustrates a detailed configuration of an image processor shown in FIG. 2.
Figure 6:
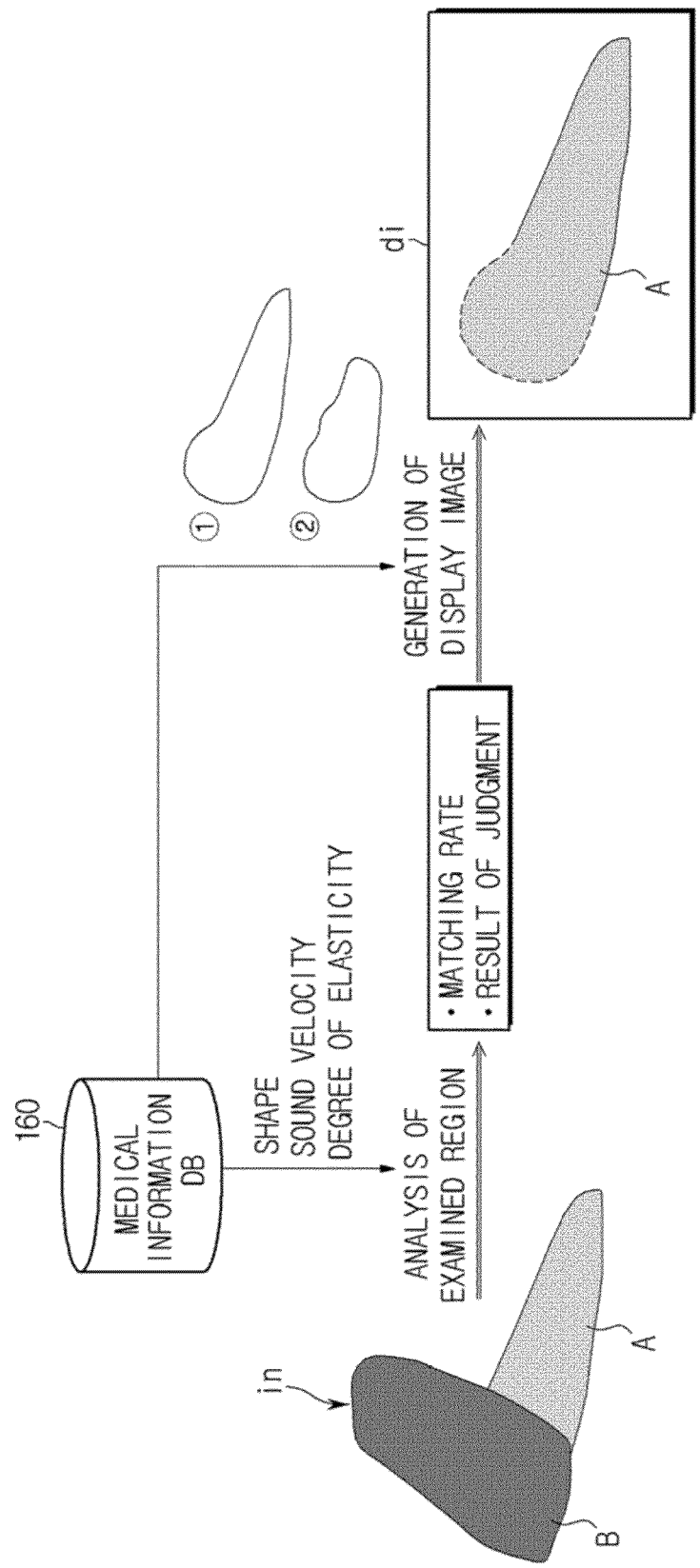
FIGS. 6, 7, and 8 are views which illustrate various examples for describing an examined region analysis process and a display image generation process applied to the ultrasonic imaging apparatus, in accordance with one or more exemplary embodiments.

The image processing unit 150 generates an ultrasonic image of the object, more particularly, an examined region (i.e., a region regarded as a target of diagnosis which is imaged via the ultrasonic probe p, with reference to item "in" of FIG. 6), and extracts various pieces of characteristic information (such as, for example, the shape of the examined region, the sound velocity of ultrasonic waves reflected by the examined region (ultrasonic echo waves), the degree of elasticity of the examined region, and/or any other suitable characteristic) which relate to the examined region by performing an analysis of the generated ultrasonic image. Further, the image processing unit 150 judges whether or not the examined region coincides with a target region (i.e., a region which is set as a target of diagnosis by a user via ultrasonic scanning) which has previously been stored in the medical information database 160 by comparing the extracted characteristic information which relates to the examined region with corresponding characteristic information which relates to the target region. Moreover, the image processing unit 150 may perform an analysis of the examined region, which analysis may include, for example, a division of the examined region into a plurality of areas and/or a detection of lesions (for example, cancerous tissues) which are present in the examined region based on the extracted characteristic information which relates to the examined region. Further, the image processing unit 150 generates a display image (i.e., a resultant image) which will be displayed on the display unit d based on a result of the judging as to whether or not the examined region coincides with the target region, a result of the analysis of the examined region, and various pieces of information which are stored in the medical information database 160. The detailed configuration and operation of the image processing unit 150 will be described below in detail with reference to FIG. 5.

The medical information database 160 includes a group of various pieces of information which are usable for judging whether or not a region which corresponds to a target of diagnosis and which is imaged by using the ultrasonic probe p, i.e., the examined region, coincides with a target region (i.e., a user-determined region) to be diagnosed via ultrasonic scanning. The medical information database 160 stores standardized ultrasonic images of various regions (e.g., organs and/or tissues) within the object ob which may be used as criteria in judging whether or not the examined region coincides with the target region, and standardized X-ray images, magnetic resonance imaging (MRI) images and computed tomography (CT) images of various regions (e.g., organs and/or tissues) within the object ob which are acquired via other medical imaging apparatuses than the ultrasonic imaging apparatus 100, such as, for example, an X-ray imaging apparatus, a magnetic resonance imaging (MRI) apparatus, a computed tomography (CT) apparatus, and/or any suitable apparatus. Further, the medical information database 160 may store characteristic information which relates to various regions (such as, for example, the heart, the liver, the breasts, the uterus, and/or any other suitable body part) within the object ob, for example, the shapes of the various regions within the object ob, the sound velocities of ultrasonic waves (ultrasonic echo waves) reflected by the various regions, and the degrees of elasticity of the various regions. Moreover, the medical information database 160 may store characteristic information which relates to various lesions (such as, for example, the degrees of elasticity of cancerous tissues) in order to detect one or more lesions which are present in regions within the object ob.

The postprocessing unit 170 may perform various postprocessing operations with respect to the ultrasonic image (display image) generated by the image processing unit 150. For example, postprocessing unit 170 may correct a luminosity, a brightness, a contrast, or a sharpness of the entirety or a part of the ultrasonic image so that a user may clearly view tissues in the ultrasonic image. Further, the postprocessing unit 170 may correct the ultrasonic image based on user directions or instructions, and/or correct the ultrasonic image based on pre-defined settings.

The storage unit 180 may temporarily or non-temporarily store an ultrasonic image. The ultrasonic image stored in the storage unit 180 may include the ultrasonic image generated by the image processing unit 170 and/or the ultrasonic image corrected by the postprocessing unit 170.

The input unit i enables a user to input instructions regarding the operation of the ultrasonic imaging apparatus 100, and the user may input any one or more of ultrasonic diagnosis start instructions, mode selection instructions for selecting one of an amplitude mode (A-mode), a brightness mode (B-mode), a motion mode (M-mode), and/or any other available mode, and an indication of a region which is desired to be diagnosed (i.e., a set region or a target region) by performing ultrasonic scanning. In particular, the input unit i may employ any one or more of various units and/or device via which a user may input data, directions or instructions, such as, for example, a keyboard, a mouse, a trackball, a tablet, and/or a touchscreen module.

The display unit d displays an ultrasonic image which is acquired during an ultrasonic diagnosis process, and/or a menu or guidance which may be required for performing an ultrasonic diagnosis. In particular, the display unit d may display a display image generated by the image processing unit 150 and a result of the analysis of the examined region. In this aspect, the display unit d may include, for example, a cathode ray tube (CRT) and/or a liquid crystal display (LCD).

Figure 4:
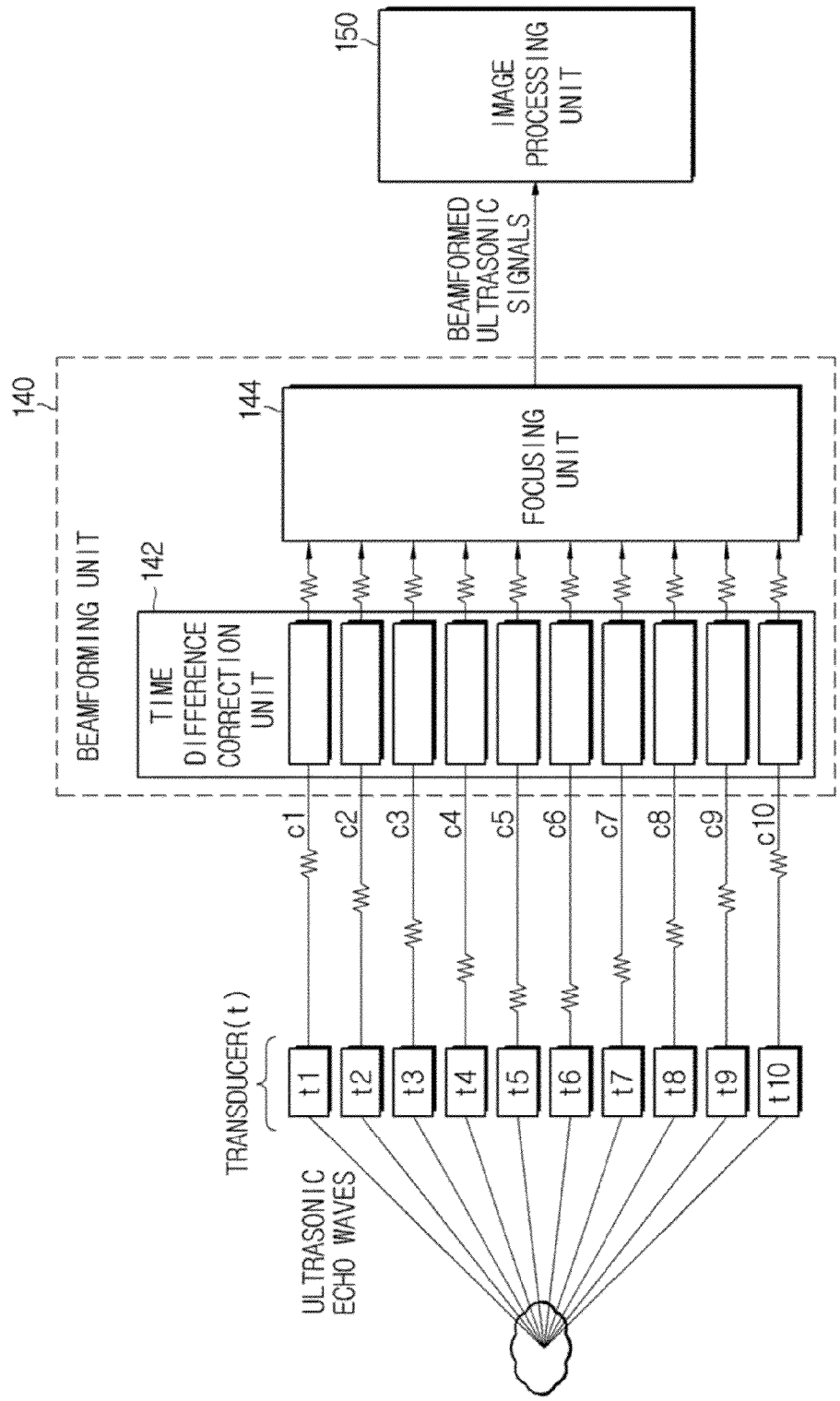
FIG. 4 is a view which illustrates a detailed configuration of a beamformer shown in FIG. 2.

FIG. 4 is a view which illustrates a detailed configuration of the beamforming unit shown in FIG. 2.

The beamforming unit 140 provided in the main body m receives ultrasonic signals c1 to c10 of a corresponding plurality of channels which signals are transmitted from the ultrasonic transducers t, focuses the received ultrasonic signals c1 to c10 of the plurality of channels, and thus outputs beamformed ultrasonic signals. The beamformed ultrasonic signals may form an ultrasonic image. In particular, the beamforming unit 140 performs beamforming of the ultrasonic signals of the plurality of channels in order to estimate the size of reflected waves in a specific space.

As exemplarily shown in FIG. 4, the beamforming unit 140 may include a time difference correction unit (also referred to herein as a "time difference corrector") 142 and a focusing unit (also referred to herein as a "focuser") 144.

The time difference correction unit 142 may correct time differences among ultrasonic signals which are output from the respective ultrasonic transducers t1 to t10.

As described above, the ultrasonic transducer t receives ultrasonic echo waves which are reflected by the target region ta. Distances between the respective ultrasonic transducers t1 to t10 which are installed at the ultrasonic probe p and the target region ta are different, but the sound velocity of ultrasonic waves are almost regular, even if it varies according to media. Therefore, the respective ultrasonic transducers t1 to t10 receive ultrasonic echo waves which are generated or reflected by the same target region ta at different times. Thus, there are designated time differences among ultrasonic signals output from the respective ultrasonic transducers t1 to t10, even if the respective ultrasonic transducers t1 to t10 receive the same ultrasonic echo waves. The time difference correction unit 142 corrects the time differences among the ultrasonic signals output from the respective ultrasonic transducers t1 to t10.

In order to correct the time differences among the ultrasonic signals, for example, the time difference correction unit 142 may delay a respective transmission of each of the ultrasonic signals c1 to c10 which are input to specific channels for a designated time based on predetermined settings, so that the ultrasonic signals c1 to c10 of the plurality of channels may be transmitted to the focusing unit 144 at the same time, as exemplarily shown in FIG. 4.

The focusing unit 144 may focus the ultrasonic signals. The focusing unit 144, as exemplarily shown in FIG. 4, may focus the ultrasonic signals of the plurality of channels, respective time differences of which have been corrected by the time difference correction unit 142.

The focusing unit 144 may focus the ultrasonic signals by selectively emphasizing or relatively attenuating signals of designated positions by applying designated weights, for example, beamforming coefficients, to each of the respective input ultrasonic signals. Thereby, an ultrasonic signal which conforms to user requirements may be generated.

Further, the focusing unit 144 may focus the ultrasonic signals by using a pre-defined beamforming coefficient which is independent with respect to the ultrasonic signals. Further, the focusing unit 144 may focus the ultrasonic signals by using a beamforming coefficient which is properly acquired based on the input ultrasonic signals.

The ultrasonic signals which are beamformed by the beamforming unit 140 are transmitted to the image processing unit 150, as exemplarily shown in FIGS. 4 and 5.

FIG. 5 is a view which illustrates a detailed configuration of the image processing unit shown in FIG. 2.

As exemplarily shown in FIG. 5, the image processing unit 150 provided within the main body m may include an image generation unit (also referred to herein as an "image generator") 152, a characteristic information extraction unit (also referred to herein as a "characteristic information extractor") 154, an examined region analysis unit (also referred to herein as an "examined region analyzer") 156, and a display image generation unit (also referred to herein as a "display image generator") 158.

The image generation unit 152 generates at least one of a 2D ultrasonic image and/or a 3D ultrasonic image of the object, more particularly, an examined region (i.e., a region which corresponds to a target of diagnosis and which is imaged by using the ultrasonic probe p, with reference to item "in" of FIG. 6), based on the ultrasonic signals focused (beamformed) by the beamforming unit 140. The image generation unit 152 may generate a 2D ultrasonic image of the examined region if the plurality of ultrasonic transducers is aligned on the ultrasonic probe p in a 1D array, and may generate a 3D ultrasonic image of the examined region if the plurality of ultrasonic transducers is aligned on the ultrasonic probe p in a 2D array.

The characteristic information extraction unit 154 extracts characteristic information which relate to the examined region by performing analysis of the 2D ultrasonic image or the 3D ultrasonic image of the examined region generated by the image generation unit 152. The characteristic information which relates to the examined region may include any one or more of the shape of the examined region, the sound velocity of ultrasonic waves (ultrasonic echo waves) reflected by the examined region, and/or the degree of elasticity of the examined region. A method of extracting the characteristic information of the examined region by performing an analysis of the input 2D or 3D ultrasonic image of the examined region is well known to those skilled in the art, and a detailed description thereof will thus be omitted.

The examined region analysis unit 156 judges whether or not the examined region coincides with a target region (i.e., a region set as a target of diagnosis by a user by performing ultrasonic scanning) by comparing the characteristic information (for example, the shape, the sound velocity, the degree of elasticity, and/or any other suitable information) which relates to the examined region extracted by the characteristic information extraction unit 154 with characteristic information which relates to the target region and which has previously been stored in the medical information database 160. Then, the examined region analysis unit 156 calculates a matching rate between the examined region and the target region based on a result of comparison between the characteristic information which relates to the examined region and the characteristic information which relates to the target region, and judges that the examined region coincides with the target region, i.e., the examined region is the same as the target region, if the calculated matching rate is greater than a predetermined value (for example, 90%). In particular, the examined region analysis unit 156 does not judge that the examined region coincides with the target region if the matching rate calculated in consideration of just one piece (for example, shape) of characteristic information from among various pieces of characteristic information is greater than the predetermined value, but judges that the examined region coincides with the target region if the matching rate calculated in consideration of at least two pieces of characteristic information from among the various pieces of characteristic information is greater than the predetermined value.

Further, the examined region analysis unit 156 may divide the examined region into a plurality of areas based on the characteristic information which relates to the examined region and which is extracted by the characteristic information extraction unit 154. For example, the examined region analysis unit 156 may divide the examined region into a plurality of areas based on a plurality of pieces of sound velocity information (represented in a corresponding plurality of ranges) which are distributed in the examined region and which are extracted by the characteristic information extraction unit 154, or divide the examined region into a plurality of areas based on a plurality of pieces of elasticity degree information (represented in a corresponding plurality of ranges) which are distributed in the examined region and which are extracted by the characteristic information extraction unit 154.

Moreover, the examined region analysis unit 156 may detect one or more lesions which are present in the examined region based on the characteristic information which relates to the examined region and which is extracted by the characteristic information extraction unit 154. In general, cancerous tissues have a lower degree of elasticity than normal tissues. Therefore, the examined region analysis unit 156 may divide the examined region into a plurality of areas based on a plurality of pieces of elasticity degree information (represented in a corresponding plurality of ranges) which are distributed in the examined region and which are extracted by the characteristic information extraction unit 154, and, if some or all of the pieces of elasticity degree information correspond to the degree of elasticity (represented in a range) of cancerous tissues, judge (i.e., detect) a corresponding area as indicating a lesion (cancerous tissues) which is present in the examined region.

The display image generation unit 158 generates a display image (i.e., a resultant image) which will be displayed on the display unit d, based on a result of the judging as to whether or not the examined region input from the examined region analysis unit 156 coincides with the target region, a result of the analysis by the examined region (i.e., the examined region which is divided into a plurality of areas and a result of the detection of one or more lesions), and various pieces of information which are stored in the medical information database 160.

Figure 7:
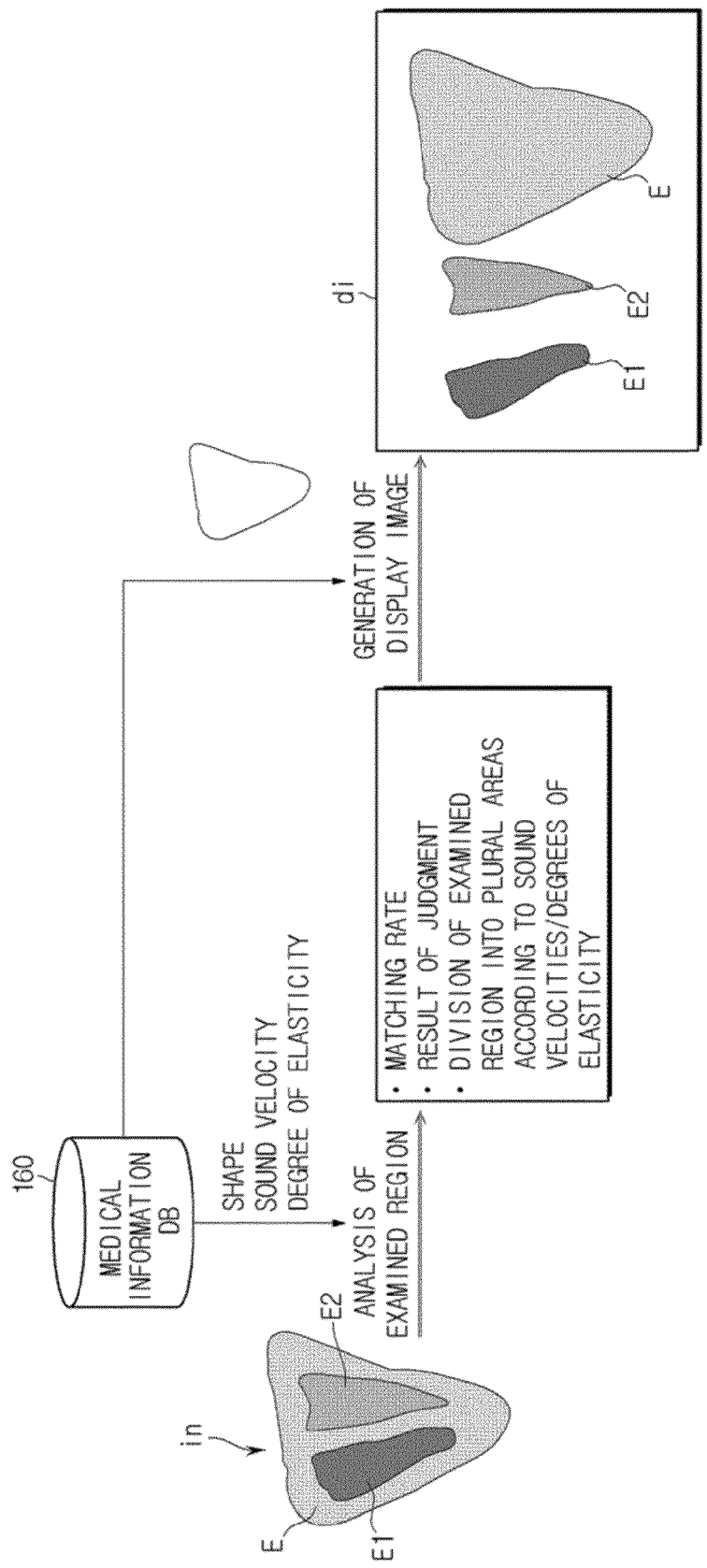
Figure 8:
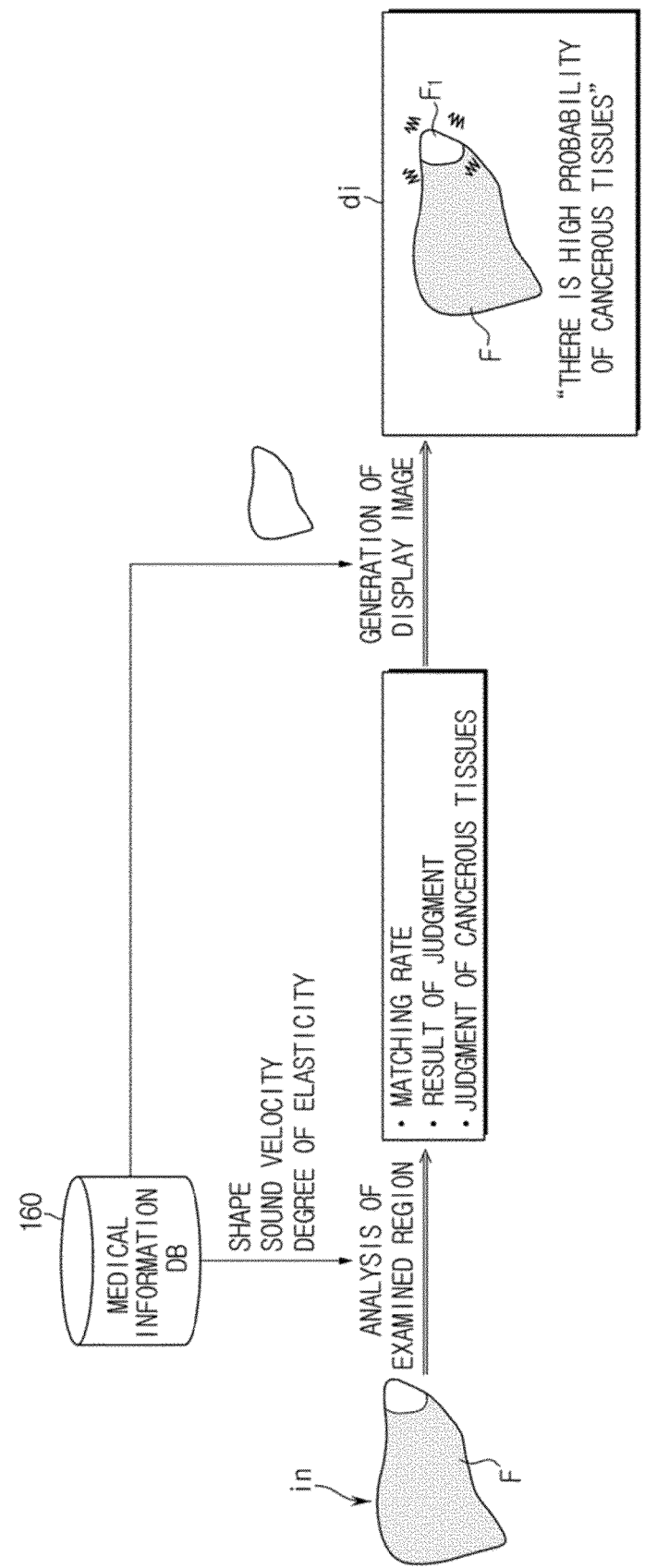

FIGS. 6, 7, and 8 are views which illustrate various examples for describing an examined region analysis process and a display image generation process applied to the ultrasonic imaging apparatus, in accordance with one or more exemplary embodiments.

FIG. 6 is a view which illustrates the examined region analysis process and the display image generation process if a plurality (i.e., at least two) of organs are imaged as an examined region.

As exemplarily shown in FIG. 6, when the examined region "in" which is extracted by the characteristic information extraction unit 154 within the image processing unit 150 is formed in the shape of two organs A and B (for example, in the shape of the outline of the two organs when one organ A overlaps with the other organ B), it is difficult to judge to which region within the object ob the examined region "in" corresponds, and it is also difficult to judge whether or not the examined region "in" coincides with the target region ta based solely upon the shape of the examined region "in". Because other pieces of characteristic information which relate to respective organs in the object ob except for the shapes of the respective organs, such as, for example, the sound velocities and the degrees of elasticity of the respective organs, are different, the examined region analysis unit 156 within the image processing unit 150 may judge whether or not the examined region "in" coincides with the target region ta based on other pieces of characteristic information (such as, for example, the sound velocity, the degree of elasticity, etc.) of the examined region except for the shape of the examined region. In the example shown in FIG. 6, the examined region corresponds to the two organs A and B. In this case, the examined region analysis unit 156 judges whether or not one of the two organs A and B coincides with the target region ta by comparing the sound velocity (and/or the degree of elasticity) which corresponds to the organ A with the sound velocity (and/or the degree of elasticity) which corresponds to the target region ta which is input by a user, read from the medical information database 160, and by comparing the sound velocity (and/or the degree of elasticity) which corresponds to the organ B with the sound velocity (and/or the degree of elasticity) which corresponds to the target region ta which is input by the user, read from the medical information database 160. If the target region ta which is input by the user is the organ A, the examined region analysis unit 156 compares the sound velocity (and/or the degree of elasticity) which corresponds to the organ A which is extracted by the characteristic information extraction unit 154 with the sound velocity (and/or the degree of elasticity) which corresponds to the organ A which is stored in the medical information database 160, calculates a matching rate of the organ A among the two organs A and B represented as the examined region "in" with respect to the target region ta based on a result of the comparison, and judges whether or not the organ A represented as the examined region coincides with the target region ta based on the calculated matching rate of the organ A with respect to the target region ta. If the calculated matching rate of the organ A represented as the examined region with respect to the target region ta is greater than a predetermined value and thus, it is judged that the organ A represented as the examined region is the same as the target region, the display image generation unit 158 generates a display image di which will be displayed on the display unit d based on a result of the judging which is input from the examined region analysis unit 156 and various pieces of information which relate to the organ A and which are stored in the medical information database 160. Because a portion of the organ A is hidden by the organ B, as exemplarily shown in FIG. 6, it is difficult to generate a display image of the organ A judged as the target region ta (i.e., a display image based on the shape of the organ A) based on the shape of the examined region "in" which is extracted by the characteristic information extraction unit 154. Therefore, as exemplarily shown in FIG. 6, the display image generation unit 158 may generate a display image di of the organ A with reference to a standardized ultrasonic image ① of the organ A, judged as the target region ta, which has previously been stored in the medical information database 160. Alternatively, the display image generation unit 158 may generate a display image di of the organ A with reference to standardized X-ray images, MRI images and CT images ② of various regions (organs) within the object ob which are acquired by using other medical imaging apparatuses than the ultrasonic imaging apparatus 100, such as, for example, an X-ray imaging apparatus, a magnetic resonance imaging (MRI) apparatus, a computed tomography (CT) apparatus, and/or any other suitable apparatus.

FIG. 7 is a view which illustrates the examined region analysis process and the display image generation process if one organ is imaged as an examined region and the organ includes a plurality of areas which have different characteristics.

As exemplarily shown in FIG. 7, when the examined region "in" which is extracted by the characteristic information extraction unit 154 within the image processing unit 150 is formed in the shape of one organ E, and the organ E includes a plurality of areas which have different characteristics, such as, for example, three areas, i.e., an area E (organ E), an area E1 (representing a part of the organ E), and an area E2 (representing another part of the organ E) which respectively correspond to sound velocities (and/or degrees of elasticity), not only an ultrasonic image based on the overall shape of a region judged as the target region ta but also ultrasonic images based on the plurality of areas which have different characteristics within the region (organ) judged as the target region ta may be displayed to a user based on user settings. In the example shown in FIG. 7, the examined region analysis unit 156 judges whether or not the organ E represented as the examined region "in" coincides with the target region ta by comparing the shape, the sound velocity, and the degree of elasticity of the organ E which are input from the characteristic information extraction unit 154 with the shape, the sound velocity, and the degree of elasticity of the target region ta which is input by the user, read from the medical information database 160. If the target region ta which is input by the user is the organ E, the examined region analysis unit 156 compares the shape, the sound velocity, and the degree of elasticity of the organ E which are extracted by the characteristic information extraction unit 154 with the shape, the sound velocity, and the degree of elasticity of the organ E which are stored in the medical information database 160, calculates a matching rate of the organ E with respect to the target region ta based on a result of the comparison, and judges whether or not the organ E coincides with the target region ta based on the calculated matching rate of the organ E represented as the examined region "in" with respect to the target region ta. Further, if a user sets the display unit d via the input unit I so that the display unit d may display not only an ultrasonic image based on the overall shape of the region judged as the target region ta but also ultrasonic images based on the plurality of areas which have different characteristics within the region (organ) judged as the target region ta, the examined region analysis unit 156 divides the examined region in into three areas, i.e., the area E (organ E), the area E1 (representing a part of the organ E), and the area E2 (representing another part of the organ E), based on corresponding sound velocities (and/or corresponding degrees of elasticity). If the matching rate of the organ E with respect to the target region ta is greater than a predetermined value and thus, it is judged that the organ E is the same as the target region ta, the display image generation unit 158 generates a display image di which will be displayed on the display unit d based on a result of the judging which is input from the examined region analysis unit 156 and various pieces of information which relate to the organ E and which are stored in the medical information database 160. Moreover, the display image generation unit 158 may generate display images di of the divided areas E1 and E2 based on information which relates to the examined region "in" which is divided into the plurality of areas based on the respective sound velocities (and/or the respective degrees of elasticity) which are input from the examined region analysis unit 156.

FIG. 8 is a view which illustrates the examined region analysis process and the display image generation process if one organ is imaged as an examined region and a lesion is present within the organ.

As exemplarily shown in FIG. 8, when the examined region "in" which is extracted by the characteristic information extraction unit 154 within the image processing unit 150 is formed in the shape of one organ F, and a lesion which has different characteristics from the characteristics of the organ F is present in the organ F, for example, cancerous tissues which have a different degree of elasticity from the degree of elasticity of the organ F are present in the organ F, not only an ultrasonic image based on the overall shape of a region judged as the target region ta, but also an ultrasonic image based on the lesion (for example, cancerous tissues) which is present in the region (organ) judged as the target region ta, may be displayed to a user. In the example shown in FIG. 8, the examined region analysis unit 156 judges whether or not one of the organ F represented as the examined region "in" coincides with the target region ta by comparing the shape, the sound velocity, and the degree of elasticity of the organ F which are input from the characteristic information extraction unit 154 with the shape, the sound velocity, and the degree of elasticity of the target region ta which is input by the user, read from the medical information database 160. If the target region ta which is input by the user is the organ F, the examined region analysis unit 156 compares the shape, the sound velocity, and the degree of elasticity of the organ F which are extracted by the characteristic information extraction unit 154 with the shape, the sound velocity, and the degree of elasticity of the organ F which are stored in the medical information database 160, calculates a matching rate of the organ F with respect to the target region ta based on a result of the comparison, and judges whether or not the organ F coincides with the target region ta based on the calculated matching rate of the organ F represented as the examined region "in" with respect to the target region ta. Further, the examined region analysis unit 156 divides the examined region in into two areas, i.e., the area F (representing the organ F) and the area F1 (representing a part of the organ F) based on corresponding degrees of elasticity, compares the degree of elasticity of the area F1 with the standardized degree of elasticity of cancerous tissues which is stored in the medical information database 160, and judges whether or not the area F1 corresponds to cancerous tissues based on a result of the comparison. If the matching rate of the organ F with respect to the target region ta is greater than a predetermined value and thus it is judged that the organ F is the same as the target region ta, and the degree of elasticity of the area F1 corresponds to the standardized degree of elasticity of cancerous tissues and thus it is judged that the area F1 corresponds to cancerous tissues, the display image generation unit 158 generates a display image di which will be displayed on the display unit d, i.e., the overall ultrasonic image of the organ F, thereby visibly displaying cancerous tissues in the organ F, based on a result of the judging which is input from the examined region analysis unit 156 (i.e., a result of the judging that the examined region coincides with the target region and that a partial area of the examined region corresponds to cancerous tissues) and various pieces of information which relate to the organ F and which are stored in the medical information database 160.

Figure 9:
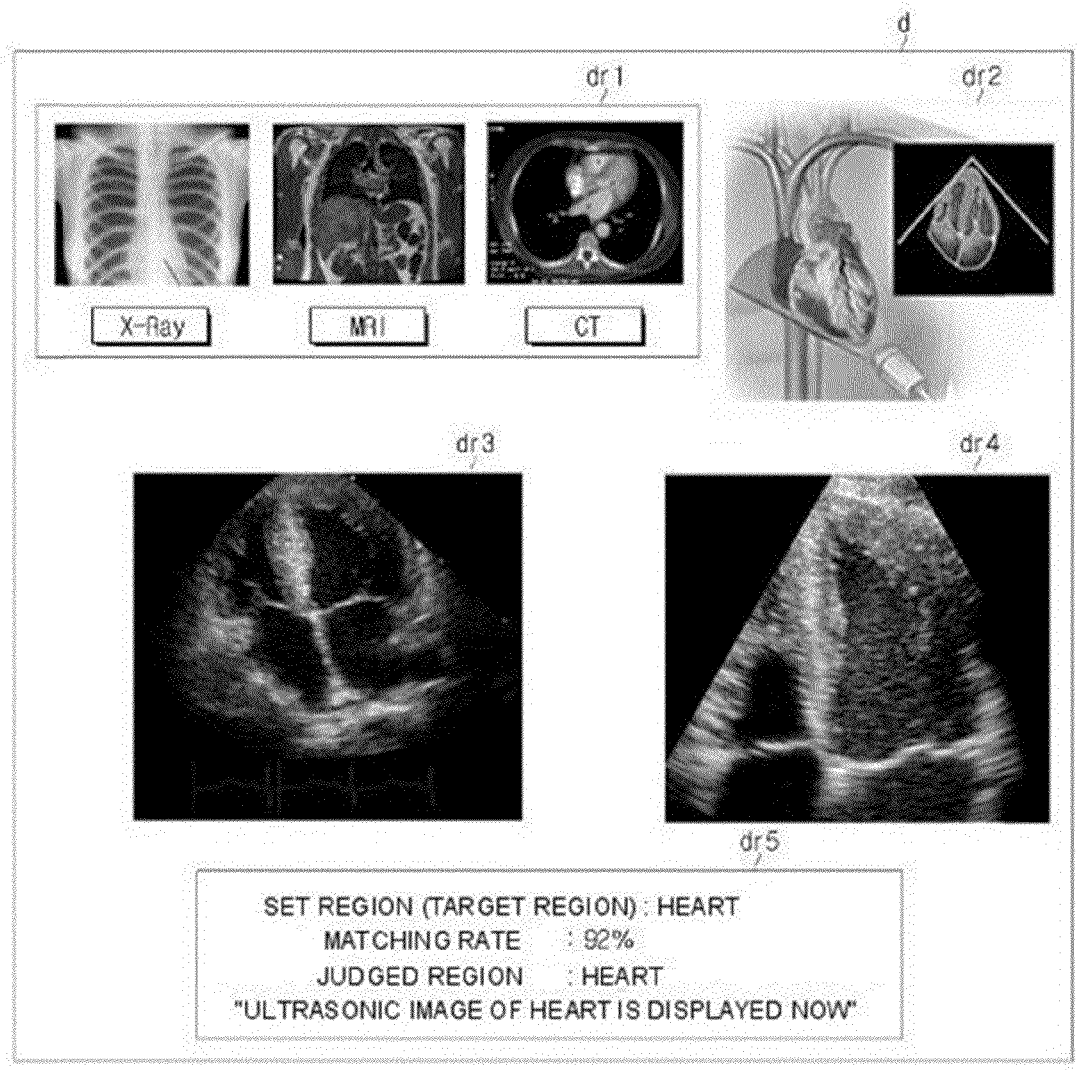
FIG. 9 is a view which exemplarily illustrates a screen of a display component displaying an ultrasonic image during imaging by a user and a result of the judgment during a diagnosis process using the ultrasonic imaging apparatus.

FIG. 9 is a view which exemplarily illustrates a screen of the display unit displaying an ultrasonic image during imaging by a user and a result of the judging during a diagnosis process which is performed by using the ultrasonic imaging apparatus.

FIG. 9 exemplarily illustrates a case in which the heart is set as a target region (i.e., a user-set region).

As exemplarily shown in FIG. 9, the display unit d is divided into five regions, i.e., a first medical image display region dr1, a guide image display area dr2, a reference ultrasonic image display region dr3, a current ultrasonic image display region dr4, and an analysis result display region dr5.

The first medical image display region dr1 displays various medical images (such as, for example, X-ray images, MRI images and CT images) which are acquired by using other medical imaging apparatuses, such as an X-ray imaging apparatus, a magnetic resonance imaging (MRI) apparatus, a computed tomography (CT) apparatus, and/or any other suitable apparatus, and serves to help a user to more intuitively view and understand the target region ta. Further, the first medical image display region dr1 displays a detailed medical image, such as a 2D or 3D image of the target region ta, as well as the overall image of the target region ta, and thus helps a general user, who may lack anatomical knowledge, to more easily understand the target region ta.

The guide image display region dr2 displays the imaging direction and how to image the target region ta by using the ultrasonic probe p to a general user, who may lack experience with respect to measuring techniques, as a moving picture or a slideshow, and thus serves to help general users to easily use the ultrasonic imaging apparatus 100.

The reference ultrasonic image display region dr3 displays a reference ultrasonic image of the target region ta which has previously been stored in the medical information database 160 for ease in performing a comparison with a current real-time ultrasonic image which is actually acquired.

The current ultrasonic image display region dr4 displays the ultrasonic image which is currently acquired in real time by a user, simultaneously displays characteristic information, such as the sound velocity and the degree of elasticity, which relates to the examined region (imaged region), and thus helps a general user to easily understand the examined region in a manner in which regions having different sound velocities and degrees of elasticity are expressed in different colors or different patterns so that the shape of the examined region may be confirmed.

The analysis result display region dr5 displays a result of the analysis which is performed by the examined region analysis unit 156. In particular, the analysis result display region dr5 displays the target region ta which is set by a user, a matching rate of the examined region "in" with respect to the target region, and a result of the judging (i.e., a judged region).

FIG. 10 is a flowchart which illustrates an image display method which is executable by using an ultrasonic imaging apparatus, in accordance with one or more exemplary embodiments.

As the initial conditions to describe the image display method, it is assumed that standardized ultrasonic images of various regions (e.g., organs and/or tissues) in an object ob and standardized X-ray images, MRI images and CT image of the various regions (e.g., organs and/or tissues) within the object which are acquired by using other medical imaging apparatuses than the ultrasonic imaging apparatus 10, which may be used as references when judging whether or not an examined region coincides with a target region, have previously been stored in the medical information database 160. Further, it is assumed that characteristic information which relates to the various regions (for example, the heart, the liver, the breasts, the uterus, etc.) within the object ob, such as, for example, the shapes of various regions within the object ob, the sound velocities of ultrasonic waves (ultrasonic echo waves) reflected by the various regions, and the degrees of elasticity of the various regions, have previously been stored in the medical information database 160. Moreover, it is assumed that characteristic information which relates to various lesions (for example, the degree of elasticity of cancerous tissues), which information may be useful for detecting one or more lesions which are present in a region within the object ob, has previously been stored in the medical information database 160.

First, in operation 210, the system control unit 110 acquires a region to be diagnosed (i.e., a user-set region or a target region) based on ultrasonic diagnosis start instructions and set information which relates to an ultrasonic diagnosis, such as, for example, mode selection instructions, from the input unit i and via ultrasonic scanning.

Next, in operation 220, the system control unit 110 controls the ultrasonic wave generation control unit 120 and the beamforming unit 140 so as to perform transmission and reception of ultrasonic signals and beamforming based on the ultrasonic diagnosis start instructions which are received via the input unit i. In particular, the system control unit 110 transmits a control signal to the ultrasonic wave generation control unit 120 so that the ultrasonic transducers t may transmit ultrasonic waves toward the object. Thereafter, the ultrasonic transducers t receive ultrasonic echo waves which are reflected by the surface of the object ob. The received ultrasonic echo waves are converted into electric signals, i.e., ultrasonic signals, and then the ultrasonic signals are output. If the plurality of ultrasonic transducers t1 to t10 receive the ultrasonic echo waves, the plurality of ultrasonic transducers t1 to t10 may output ultrasonic signals c1 to c10 of a corresponding plurality of channels. Time differences among the output ultrasonic signals c1 to c10 of the plurality of channels are corrected by the time difference correction unit 142 within the beamforming unit 140, and the ultrasonic signals, time differences of which have been corrected by the time difference correction unit 142, are focused by the focusing unit 144. As a result, the beamformed ultrasonic signals are output.

Thereafter, in operation 230, the image generation unit 152 within the image processing unit 150 generates at least one of a 2D ultrasonic image and/or a 3D ultrasonic image of the object ob, more particularly, the examined region "in", based on the ultrasonic signals focused (beamformed) by the beamforming unit 140.

Next, in operation 240, the characteristic information extraction unit 154 within the image processing unit 150 extracts characteristic information which relates to the examined region "in" by performing an analysis of the 2D ultrasonic image and/or the 3D ultrasonic image of the examined region "in" generated by the image generation unit 152. The characteristic information which relates to the examined region may include any one or more of the shape of the examined region, the sound velocity of ultrasonic waves (ultrasonic echo waves) reflected by the examined region, and the degree of elasticity of the examined region.

Thereafter, in operation 250, the examined region analysis unit 156 within the image processing unit 150 compares the characteristic information (for example, the shape, the sound velocity, the degree of elasticity, etc.) which relates to the examined region "in" and which is extracted by the characteristic information extraction unit 154 with characteristic information which relates to the target region ta and which is previously stored in the medical information database 160, and then, in operation 260, calculates a matching rate of the examined region "in" with respect to the target region ta based on a result of the comparison.

Next, in operation 270, the examined region analysis unit 156 judges whether or not the calculated matching rate of the examined region "in" with respect to the target region ta is greater than a predetermined value. Upon judging that the calculated matching rate of the examined region "in" with respect to the target region ta is not greater than the predetermined value (in accordance with a "No" result of operation 270), the examined region analysis unit 156 returns to operation 250, and continuously compares the characteristic information which relates to the examined region "in" and which is extracted by the characteristic information extraction unit 154 with characteristic information which relates to the target region ta and which is previously stored in the medical information database 160.

Conversely, upon judging that the calculated matching rate of the examined region "in" with respect to the target region ta is greater than the predetermined value (in accordance with a "Yes" result of operation 270), in operation 280, the examined region analysis unit 156 judges that the examined region "in" coincides with the target region ta, i.e., judges the examined region "in" as the target region ta.

Upon judging that the examined region in coincides with the target region ta, in operation 290, the display image generation unit 158 within the image processing unit 150 generates a display image which will be displayed on the display unit d based on a result of the analysis by the examined region analysis unit 156 and the characteristic information which is stored in the medical information database 160.

Thereafter, in operation 300, the system control unit 110 transmits a control signal to the display unit d so that the display unit d may display the display image generated by the display image generation unit 150 and the result of analysis by the examined region analysis unit 156.

As is apparent from the above description, an ultrasonic imaging apparatus and an image display method thereof in accordance with at least one exemplary embodiment may be used in order to more accurately judge to which region within an object an examined region corresponds based on various pieces of characteristic information of the examined region which are extracted as a result of an analysis of an ultrasonic image.

Further, the ultrasonic imaging apparatus and the image display method thereof display various medical images (for example, any one or more of an X-ray image, an MRI image and a CT image) acquired via other medical imaging apparatuses, such as an X-ray imaging apparatus, a magnetic resonance imaging (MRI) apparatus, a computed tomography (CT) apparatus, etc., as well as the ultrasonic image acquired by an ultrasonic probe, thus facilitating a more intuitive understanding of the examined region by a user.

Further, the ultrasonic imaging apparatus and the image display method thereof display various medical images together with a result of a judgment as to whether or not the examined region coincides with a target region, thus facilitating an obtaining of an image of a desired target region by a general user lacking anatomical knowledge or measuring techniques.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An ultrasonic imaging apparatus comprising:
an ultrasonic probe configured to transmit ultrasonic signals toward an object and to receive ultrasonic signals reflected by the object;
a beamformer configured to perform beamforming based on the ultrasonic signals received by the ultrasonic probe; and
an image processor configured to generate an ultrasonic image of an examined region within the object based on a result of the beamforming, to extract characteristic information which relates to the examined region from the generated ultrasonic image, and to judge whether or not the examined region coincides with a target region based on the extracted characteristic information.

2. The ultrasonic imaging apparatus according to claim 1, wherein the examined region includes a region which corresponds to a target of a diagnosis which is imaged by using the ultrasonic probe, and the target region includes a region which is set by a user.

3. The ultrasonic imaging apparatus according to claim 2, further comprising a medical information database configured to store at least one from among standardized ultrasonic images of a plurality of regions within the object, standardized X-ray images, magnetic resonance imaging (MRI) images and computed tomography (CT) images of the plurality of regions within the object, first characteristic information which relates to the plurality of regions within the object, and second characteristic information which relates to a plurality of lesions and which is usable for detecting one or more lesions which are present in the examined region within the target object.

4. The ultrasonic imaging apparatus according to claim 3, wherein the first characteristic information includes at least one from among a shape of one or more of the plurality of regions, a sound velocity of at least one ultrasonic wave reflected by one or more of the plurality of regions, and a degree of elasticity of one or more of the plurality of regions.

5. The ultrasonic imaging apparatus according to claim 4, wherein the image processor includes:
an image generator configured to generate at least one from among a two-dimensional (2D) ultrasonic image and a three-dimensional (3D) ultrasonic image of the examined region based on the result of the beamforming;
a characteristic information extractor configured to extract third characteristic information which relates to the examined region by performing analysis of the generated at least one from among the 2D ultrasonic image and the 3D ultrasonic image of the examined region; and
an examined region analyzer configured to judge whether or not the examined region coincides with the target region by comparing the extracted third characteristic information which relates to the examined region with the first characteristic information which relates to the target region and which is stored in the medical information database.

6. The ultrasonic imaging apparatus according to claim 5, wherein the examined region analyzer is further configured to calculate a matching rate between the examined region and the target region based on a result of the comparing of the third characteristic information with the first characteristic information, and to judge that the examined region coincides with the target region if the calculated matching rate is greater than a predetermined value.

7. The ultrasonic imaging apparatus according to claim 6, wherein the examined region analyzer is further configured to divide the examined region into a plurality of areas based on the extracted third characteristic information which relates to the examined region.

8. The ultrasonic imaging apparatus according to claim 7, wherein the examined region analyzer is further configured to detect at least one lesion which is present in the examined region based on the extracted third characteristic information which relates to the examined region.

9. The ultrasonic imaging apparatus according to claim 8, wherein the image processor further includes a display image generator configured to generate a display image based on a result of the judging as to whether or not the examined region coincides with the target region, the examined region divided into the plurality of areas, a result of the detecting of the at least one lesion, and various pieces of information which is stored in the medical information database.

10. The ultrasonic imaging apparatus according to claim 9, further comprising a display component configured to display the display image,
wherein the display component includes:
a first medical image display region configured to display at least one from among a standardized X-ray image, an MRI image, and a CT image of the examined region judged as the target region;
a guide image display region configured to display a guide image so as to facilitate a use of the ultrasonic probe with respect to the target region;
a reference ultrasonic image display region configured to display a reference ultrasonic image of the target region so as to facilitate a comparison with a currently acquired real-time ultrasonic image;
a current ultrasonic image display region configured to display the currently acquired real-time ultrasonic image; and
an analysis result display region configured to display a result of the judging performed by the examined region analyzer.

* * * * *